United States Patent [19]
Bunel et al.

[11] Patent Number: 5,847,191
[45] Date of Patent: Dec. 8, 1998

[54] PROCESS FOR THE HYDROCYANATION OF MONOOLEFINS USING BIDENTATE PHOSPHITE LIGANDS AND ZERO-VALENT NICKEL

[75] Inventors: Emilio Enrique Bunel, Wilmington; Kenneth C. McNulty, Rockland, both of Del.

[73] Assignee: E. I. du Pont de Nemours and Company, Wilmington, Del.

[21] Appl. No.: 902,438

[22] Filed: Jul. 29, 1997

[51] Int. Cl.⁶ .................................................. C07C 253/00
[52] U.S. Cl. .............................................................. 558/338
[58] Field of Search ............................................. 555/338

[56] References Cited

U.S. PATENT DOCUMENTS

| | | | |
|---|---|---|---|
| 3,496,215 | 2/1970 | Drinkard et al. | 260/465.8 |
| 3,496,217 | 2/1970 | Drinkard, Jr. et al. | 260/465.8 |
| 3,496,218 | 2/1970 | Drinkard, Jr. et al. | 260/465.8 |
| 3,631,191 | 12/1971 | Kane et al. | 260/439 R |
| 3,655,723 | 4/1972 | Drinkard, Jr. et al. | 260/465.3 |
| 3,766,237 | 10/1973 | Drinkard, Jr. et al. | 260/465.3 |
| 3,773,809 | 11/1973 | Walter | 260/465.8 R |
| 4,082,811 | 4/1978 | Shook, Jr. | 260/606.5 |
| 4,087,452 | 5/1978 | Kuntz | 558/338 |
| 4,339,395 | 7/1982 | Barnette et al. | 260/465.8 R |
| 4,774,353 | 9/1988 | Hall et al. | 558/335 |
| 4,874,884 | 10/1989 | McKinney et al. | 558/338 |
| 5,512,695 | 4/1996 | Kreutzer et al. | 558/338 |
| 5,512,696 | 4/1996 | Kreutzer et al. | 558/338 |
| 5,523,453 | 6/1996 | Breikss | 558/338 |

FOREIGN PATENT DOCUMENTS

| | | | |
|---|---|---|---|
| 0 633 062 A1 | 4/1994 | European Pat. Off. | B01J 31/16 |
| 93/03839 | 3/1993 | WIPO | B01J 31/24 |
| 95/14659 | 6/1995 | WIPO | C07C 253/10 |

OTHER PUBLICATIONS

Michael J. Baker et al., Chelating Diphosphite Complexes of Nickel(0) and Platinum (0): Their Remarkable Stability and Hydrocyanation Activity, *J. chem. Soc. Chem. Commun.*, 803–804, 1991.

Michael J. Baker and Paul G. Pringle, Chiral Aryl Diphosphites: a New Class of Ligands for Hydrocyanation Catalysis, *J. Chem. Soc., Chem. Commun.*, 1292–1293, 1991.

C.A. Tolman et al., Homogeneous Nickel–Catalyzed Olefin Hydrocyanation, *Advances in Catalysis*, 33, 1–46, 1985.

*Primary Examiner*—Johann Richter
*Assistant Examiner*—Joseph Murray

[57] ABSTRACT

The present invention provides a process for hydrocyanation comprising reacting a nonconjugated, ethylenically unsaturated compound in a two phase process solvent with HCN in the presence of a Lewis acid promoter and a catalyst system comprising zero-valent nickel and an organic phosphorous containing ligand having the structure $(PR_2)_n R'$ where n is an integer from 1 to 2, R and R' are organic residues which may be the same or different and where the R or R' contain at least one C9 to C40 aliphatic group positioned as a tail extending away from the primary ligand structure rendering the ligand lipophilic.

14 Claims, No Drawings

PROCESS FOR THE HYDROCYANATION OF MONOOLEFINS USING BIDENTATE PHOSPHITE LIGANDS AND ZERO-VALENT NICKEL

FIELD OF THE INVENTION

The invention generally relates to a process useful for the hydrocyanation of an ethylenically unsaturated compounds in the presence of a Lewis Acid promoter and a catalyst system comprising zero-valent nickel and an organic phosphorous containing ligand having the structure $(PR_2)_nR'$ where n is an integer from 1 to 2, R and R' are organic residues which may be the same or different and where the R or R' contain at least one C9 to C40 aliphatic group positioned as a tail extending away from the primary ligand structure rendering the ligand lipophilic.

BACKGROUND OF THE INVENTION

Hydrocyanation catalyst systems, particularly pertaining to the hydrocyanation of olefins, are known in the art. For example, systems useful for the hydrocyanation of butadiene to form pentenenitrile (PN) and in the subsequent hydrocyanation of the pentenenitrile (PN) to form adiponitrile (ADN) are known in the commercially important nylon synthesis field.

The hydrocyanation of olefins using transition metal complexes with monodentate phosphite ligand is documented in the prior art. See for example; U.S. Pat. Nos. 3,496,215, 3,631,191, 3,655,723, and 3,766,237, and Tolman, C. A.; McKinney, R. J.; Seidel, W. C.; Druliner, J. D.; and Stevens, W. R. in Catalysis, 33, 1, 1985.

The hydrocyanation of activated olefins such as conjugated olefins (e.g., butadiene and styrene) and strained olefins (e.g., norborene) proceeds without the use of a Lewis Acid promoter, while hydrocyanation of unactivated olefins such as 1-octene and 3-pentenenitrile requires the use of a Lewis Acid promoter. Teachings regarding the use of a promoter in the hydrocyanation reaction appear, for example, in U.S. Pat. No. 3,496,217. This patent discloses an improvement in hydrocyanation using a promoter selected from a large number of metal cation compounds with a variety of anions as catalyst promoters.

U.S. Pat. No. 3,496,218 discloses a nickel hydrocyanation catalyst promoted with various boron-containing compounds, including triphenylboron and alkali metal borohydrates. U.S. Pat. No. 4,774,353 discloses a process for the preparation of dinitriles, including ADN, from unsaturated nitrites, including PN, in the presence of a zero-valent nickel catalyst and a triorganotin catalyst promoter. U.S. Pat. No. 4,874,884 discloses a process for producing ADN by the zero-valent nickel catalyzed hydrocyanation of pentenenitriles in the presence of a synergistic combination of promoters selected in accordance with the reaction kinetics of the ADN synthesis.

Use of bidentate phosphorous ligands similar to those used in the present invention have been disclosed in the literature for the hydrocyanation of both activated and unactivated olefins. Such publications include: Baker, M. M. and Pringle, P. G.; J. Chem. Soc., Chem. Commun. 1292, 1991; Baker, M. J.; Harrison, K. N.; Orpen, A. G.; Pringle, P. G.; and Shaw, G.; J. Chem. Soc., Chem. Commun., 803, 1991, WO/93/03839 and WO/95/14659.

These prior patents teach catalyst structures and improvements in continuous processes for hydrocyanation, but none address the problem of isolating product, byproduct and catalyst one from the other. Yet, in all hydrocyanation processes the catalyst must be separated from the reaction products. U.S. Pat. Nos. 3,773,809; 4,082,811 and 4,339,395 teach processing techniques for the isolation of the hydrocyanation reactants, products and catalyst system. U.S. Pat. No. 3,773,809 teaches a control of the ratio of the product mononitrile to the product dinitriles such that the reaction mixture is two phase. U.S. Pat. No. 4,433,395 teaches the addition of ammonia to aid in the separation of products, reactants and the catalyst system. U.S. Pat. No. 4,082,811 teaches the precipitation of the catalyst as a means to recover it from the process mixture.

The present invention provides a process by which the reaction products, including high boiling products and byproducts may be easily separated from the reaction catalyst system. In the present process the catalyst system may be readily separated from reaction products and recycled for use in the process thus providing longer active catalyst system productivity.

SUMMARY OF THE INVENTION

The present invention provides a process for hydrocyanation comprising reacting a nonconjugated, ethylenically unsaturated compound in a reaction solvent with HCN in the presence of a Lewis acid promoter and a catalyst system comprising a zero valent nickel compound and an organic phosphorous containing ligand having the structure $(PR_2)_nR'$ where n is an integer from 1 to 2, R and R' are organic residues which may be the same or different and where the R or R' contain at least one C9 to C40 aliphatic group positioned as a tail extending away from the primary ligand structure rendering the ligand lipophilic. The reaction solvent is a two phase mixture of an organic compound having from 5 to 20 carbon atoms and polar solvent. The most preferred ligands are bidentate phosphites, $(POR_2)_2OR'$, where at least one C9 to C40 aliphatic group positioned on the backbone or side arm ring structures of the ligand.

The present process may be represented as a series of process steps comprising:

(a) reacting the ethylenically unsaturated compound in a reaction solvent to form a reaction mixture with HCN in the presence of Lewis acid promoter and a catalyst system composed of a zero valent nickel compound and an organic phosphorous containing ligand having the structure $(PR_2)_nR'$ where n is an integer from 1 to 2, R and R' are organic residues which may be the same or different and where the R or R' contain at least one C9 to C40 aliphatic group positioned as a tail extending away from the primary ligand structure rendering the ligand lipophilic;

(b) adding a non-polar solvent to the reaction mixture to form two phases, one a polar phase predominately formed from the reaction products and one formed predominately from the non-polar solvent and the catalyst system such that the reaction products including the high boiling reaction products of the hydrocyanation remain in the polar phase and the catalyst system is partitioned substantially into the non-polar phase; and (c) separating the two phases and isolating the reaction products from the polar phase and the catalyst from the non-polar phase.

The preferred ligand is a bidentate phosphite ligand having the structure $(POR_2)_2OR'$ where R and R' are organic residues and where the R or R' contain at least one C9 to C20 aliphatic group positioned as a tail extending away from the bridging group (R') or the side arms (R) rendering the ligand lipophilic.

Volatiles may be removed in the present process from the reaction mixture of step (a) before the addition of the non-polar solvent of step (b). Also in the present process steps (a) and (b) may be combined so that the hydrocyanation is carried out in a two phase reaction solvent.

The present process may be run as a batch or a continuous process. In a continuous process the recovered catalyst is returned to step (a) and the steps are repeated.

The present process also provides an improved hydrocyanation process where a nonconjugated, ethylenically unsaturated compound is reacted with HCN in the presence of a Lewis acid promoter and a catalyst system composed of a zero valent nickel compound and a bidentate organic phosphorous containing ligand wherein the ethylenically unsaturated compound also functions as reaction solvent, the improvement comprising: forming the catalyst system from the ligand having the structure $(PR_2)_nR'$ where n is an integer from 1 to 2, R and R' are organic residues which may be the same or different and where the R or R' contain at least one C9 to C40 aliphatic group positioned as a tail extending away from the primary ligand structure rendering the ligand lipophilic; and following hydrocyanation of the ethylenically unsaturated compound adding to the reaction mixture a two phase solvent mixture consisting of a polar and a non-polar phase so that the reaction products of the hydrocyanation are extracted into the polar phase of the solvent mixture and the catalyst system remains substantially in the non-polar phase of the solvent mixture.

Preferred structures for the ligands of the present invention are Ligands I–III as noted below:

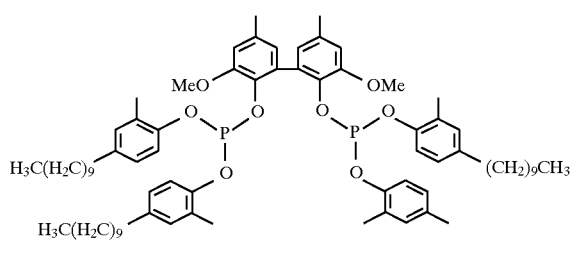

Ligand I

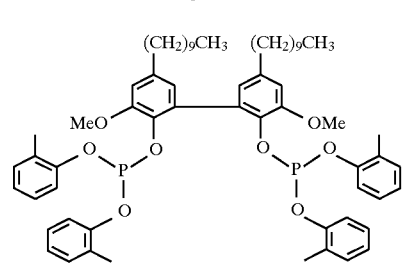

Ligand II

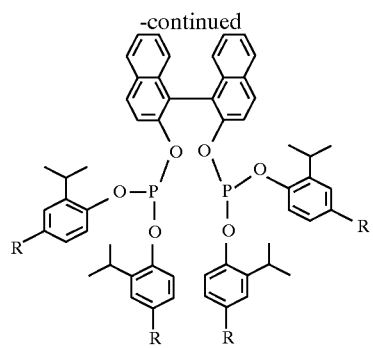

Ligand III where in Ligand III R is either $CO(CH_2)_8CH_3$ or $(CH_2)_9CH_3$.

DETAILED DESCRIPTION OF THE INVENTION

The present invention provides a process for hydrocyanation, comprising reacting a nonconjugated ethylenically unsaturated compound with hydrogen cyanide in the presence of a Lewis Acid promoter and a catalyst system comprising a zero valent nickel compound and an organic phosphorus containing ligand having the structure $(PR_2)_nR'$ where n is an integer from 1 to 2, R and R' are organic residues which may be the same or different and where the R or R' contain at least one C9 to C40 aliphatic group positioned as a tail extending away from the primary ligand structure rendering the ligand lipophilic. The most preferred ligands are bidentate phosphites having at least one C9 to C40 aliphatic group positioned as a tail extending away from the bridging group (R') or the side arms (R) rendering the ligand lipophilic. The term lipophilic when used to modify the term ligand means that the ligand, in a two phase solvent system formed by mixing a polar with a non-polar solvent, will be substantially distributed in the non-polar phase.

The present process combines a ligand structure and a two phase process solvent that allows the easy isolation of reaction products and byproducts from the catalyst system. The term process solvent as used herein means a solvent, added initially to the reaction as the reaction solvent, or a solvent or a mixture of solvents added following the reaction that is used to extract and separate components of the reaction system. The term extraction means the preferential partitioning or distribution of a compound in one of two immiscible liquid phases.

A suitable starting material for the present process are nonconjugated acyclic aliphatic mono-olefins substrates containing from 2 to approximately 30 carbon atoms having at least one nonconjugated aliphatic carbon-carbon double bond. 3-Pentenenitrile, 4-pentenenitrile and alkyl-3-pentenoate are preferred. In the case of alkyl-3-pentenoate, the alkyl group is preferably C1–C6. Most preferably, the alkyl group is methyl. 3-Pentenenitrile and 4-pentenenitrile are especially preferred. As a practical matter, when the nonconjugated acyclic aliphatic mono-olefins are used in accordance with this invention, up to about 10% by weight of the mono-olefin may be present in the form of a conjugated isomer, which itself may be subject to hydrocyanation. For example, when 3-pentenenitrile is used, as much as 10% by weight may be 2-pentenenitrile. Suitable unsaturated compounds include olefins and olefins substituted with groups which do not attack the catalyst, such as cyano.

These unsaturated compounds include monoolefins containing 2 to 30 carbon atoms such as ethylene, propylene, butene-1, pentene-2, hexene-2, etc., nonconjugated diolefins such as allene, and substituted compounds such as 3-pentenenitrile, 4-pentenenitrile, and methyl-3-pentenoate.

The present hydrocyanation process may be carried out by charging a reactor with all of the reactants, or preferably the reactor is charged with the catalyst precursor or catalyst components, the unsaturated organic compound, the promoter, and any solvent to be used. The hydrogen cyanide is added slowly. HCN may be delivered as a liquid or as a vapor to the reaction. Another technique is to charge the reactor with the catalyst, promoter, and any solvent to be used, and feed both the unsaturated compound and the HCN to the reaction mixture. The molar ratio of the unsaturated compound to catalyst generally is varied from about 10:1 to 2000:1.

Preferably the reaction medium is agitated, such as by stirring or shaking. The cyanated product can be recovered by conventional techniques such as distillation. The reaction may be run either batchwise or in a continuous manner.

The exact temperature which is preferred is dependent to a certain extent on the particular catalyst being used, the particular unsaturated compound being used, and the desired rate. Generally, temperatures of from −25° C. to 200° C. can be used with from 0° to 150° C. being preferred.

Atmospheric pressure is satisfactory for carrying out the present invention and, hence, pressure of from about 0.05 to 10 atmospheres are preferred due to the obvious economic considerations, although pressures of from about 0.05 to 100 atmospheres can be used if desired.

The zero-valent nickel can be prepared or generated according to techniques well known in the art (U.S. Pat. Nos. 3,496,217, 3,631,191, 3,846,461, 3,847,959, and 3,903,120 which are incorporated by reference). Zero-valent nickel compounds that contain ligands which can be displaced by the organophosphorous ligand are a preferred source of zero-valent nickel. Two such preferred zero-valent nickel compounds are $Ni(COD)_2$ (COD is 1,5-cyclooctadiene) and $Ni(P(O-O-C_6H_4CH_3)_3)_2(C_2H_4)$, both of which are known in the art. Alternatively, divalent nickel compounds may be combined with a reducing agent, and are then able to serve as suitable sources of zero-valent nickel in the reaction. Suitable divalent nickel compounds include compounds of the formula $NiY2$ where Y is a halide, carboxylate, or acetylacetonate. Suitable reducing agents include metal borohydrides, metal aluminum hydrides, metal alkyls, Zn, Fe, Al, Na, or $H_2$. Elemental nickel, preferably nickel powder, when combined with a halogenated catalyst, as described in U.S. Pat. No. 3,903,120, is also a suitable source of zero-valent nickel.

Typically the process of the present invention run in the presence of one or more Lewis acid promoters which may affect the activity and the selectivity of the catalyst system. The promoter may be an inorganic or organometallic compound in which the cation is selected from the group consisting of scandium, titanium, vanadium, chromium, manganese, iron, cobalt, copper, zinc, boron, aluminum, yttrium, zirconium, niobium, molybdenum, cadmium, rhenium and tin.

The formation of nitrites by hydrocyanation, particularly, in a continuous process, often times produces high boiling products that are formed from the condensation of the nitrile reaction products. These high boiling materials are particularly difficult to remove from the catalyst reaction system. In some cases the desired product may, itself, be high boiling and difficult to separate from the catalyst system. The present invention provides, through the proper selection of the ligand structure for the catalyst system and the selective use of solvents, a process in which the high boiling reaction products and byproducts may be easily separated from the catalyst system.

Although the ligand of the present invention may be monodentate or bidentate, the preferred ligands of the present invention are bidentate organic ligand having two trivalent phosphorous atoms wherein the ligand contains at least one C9 to C40 aliphatic group positioned on the backbone or side arm ring structures of the ligand. Bidentate ligands having two trivalent phosphorous may be of the class of phosphine, phosphite, phosphinite, or phosphonite.

Particularly preferred ligands are bidentate organic phosphite ligands having at least one C9 to C40 aliphatic group positioned on the backbone or side arm ring structures of the ligand. Especially preferred are ligands having the structure:

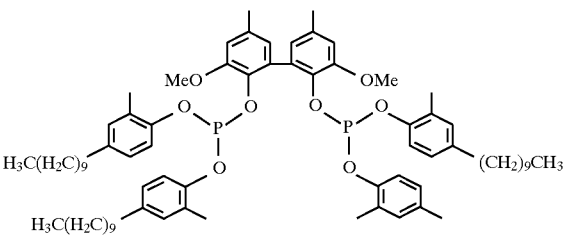

Ligand I

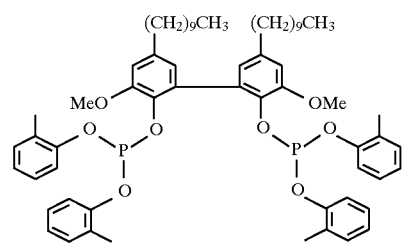

Ligand II

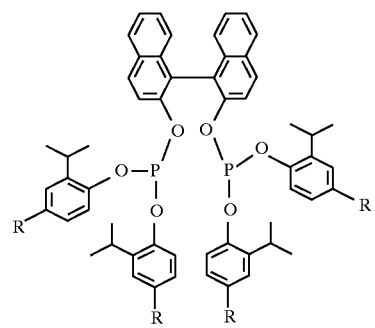

Ligand III wherein Ligand III R is either $CO(CH_2)_8CH_3$ or $(CH_2)_9CH_3$.

The structure of any ligand used in a hydrocyanation catalyst system is generally selected such that backbone and side arms of the ligand structure provide the desired selectivity and activity. The term backbone refers to the bridging group between the two phosphorus atoms and the term side arms refer the non-bridging groups attached to the phosphorus atoms.

Many backbone and side arm structures of bidentate ligands known for hydrocyanation may be modified for use in the present invention by adding to the ligand at least one C9 to C40 aliphatic group substituted for a hydrogen or some R group of the aromatic ring backbone or side arm structure. Also ligands known for hydrocyanation that already have at least one C9 to C40 aliphatic group on the backbone or side arm structures of the ligand may be used in the present invention. By the term modifying is meant the substitution of the aliphatic group of the invention on a ligand already synthesized or changing the synthesis of the ligand so that the final structure contains at least one C9 to C40 aliphatic group.

The ligand structures of the present invention provide long chain aliphatic group or tails that extend from the ligand structure causing the ligand to become preferentially soluble in a non-polar solvent. The substitution of the aliphatic group on a backbone or side arm position will contribute little if any to a change in the activity or selectivity of the ligand as used in the catalyst system for hydrocyanation. Thus by adapting the ligand to be preferentially soluble in a non-polar solvent, the present invention provides a ligand property that can work together with the two phase process solvent to make the separation of ligand and product simple and easy, while maintaining the activity and selectivity of the basic ligand structure (that is the activity and selectivity of the ligand not having the substitution of a smaller group by a C9 to C40 aliphatic group).

The second aspect of the present invention is the use of a two phase process solvent. As described below the two phase solvent mixture or process solvent may be used in three ways in the practice of the present invention. It may be used as the reaction solvent; or one of the components of the two phase solvent mixture may be used as the reaction solvent for the hydrocyanation reaction, and then the other component added following the hydrocyanation to serve to extract and separate products from the catalyst system; or the hydrocyanation reaction may be carried out with the ethylenically unsaturated compound also functioning as the reaction solvent; then following the hydrocyanation, the two phase process solvent is added to the reaction mixture to extract and separate products from the catalyst system.

Generally when one solvent does not dissolve in another solvent, or when a first solvent has a low or limited solubility in a second solvent, the two solvents are said to be immiscible. When immiscible solvents are mixed together, they separate into two phases—the less dense phase floating on the more dense phase. Also generally, when a mixture of two or more solvents form separate phases one phase is said to polar relative to the other. Polar and non-polar are relative terms, but polar solvents are generally those that contain electronegative atoms such as oxygen or nitrogen, are of lower molecular weights and mix with water. Non-polar solvents are those that contain primarily hydrogen and carbon, that do not mix with water but that mix readily with oil. As used herein, the term polar means to hydrophilic or lipophobic; while the term non-polar means hydrophobic or lipophilic. Thus, a lipophilic ligand is one that is preferentially soluble in a non-polar solvent or in the more non-polar of a two solvent mixture.

To form the two phase process solvent of the present invention, one mixes a polar and a non-polar solvent or mixtures of polar and non-polar solvents to form two phases. One phase is more lipophilic than the other. As described above, this two phase solvent mixture may be present as the initial reaction solvent for the hydrocyanation. It may be added as a two phase mixed solvent following the hydrocyanation as an extraction medium. Or a single solvent may be added to the reaction mixture causing the formation of a two phase mixture from which the desired component of the hydrocyanation reaction system may be isolated.

In selecting solvent components for the two phase solvent mixture, it is only essential that the two components form two separate phases when mixed together. The ligand structures of the present invention, having extended aliphatic tails that may be as long as C40, cause the ligand to be preferentially soluble in the non-polar component of the two phase solvent mixture. The present invention also allows for the adjustment of the polarity of the ligand by the choice of longer tails and a greater number of tails being used to provide a more non-polar ligand.

Examples of polar compounds suitable for forming the two phase solvent mixture include water, dimethylacetamide (DMAc), dimethyl sulfoxide (DMSO), methanol, ethanol, dimethylformamide (DMF), acetonitrile, adiponitrile (ADN) N-methyl pyrrolidone(NMP).

Compounds such as C5 to C20 hydrocarbons including linear, branched, cyclic or aromatic compounds are examples of compounds that may be used as the non-polar component. Higher molecular weight alcohols, aldehydes, esters or ketones may also be used as the non-polar component. Examples of non-polar compounds suitable in the process of the present invention include hexane, cyclohexane, hexene, petroleum ethers and naphta. For an aromatic solvent used in the practice of the present invention, it is preferred that the aromatic solvent molecule have aliphatic side chains to ensure that it is non-polar enough to form a second phase when mixed with the reaction products of the hydrocyanation.

If the reaction conditions are at sufficient pressure, even C4 hydrocarbons could be used as the non-polar component of the solvent mixture.

In the practice of the present invention, a polar solvent may be added to the reaction mixture after the hydrocyanation reaction is completed but before any products are isolated from the mixture. Such a process would occur as follows: (a) reacting the ethylenically unsaturated compound with HCN in the presence of Lewis acid promoter and a catalyst system composed of a zero valent nickel compound and a ligand of the present invention in a reaction solvent to form a reaction mixture, (b) adding a non-polar solvent to the reaction product of step (a) so that two phases are formed and allowing the catalyst system to be extracted into the non-polar solvent, (c) isolation of the non-polar solvent layer, (d) evaporation of the non-polar solvent to isolate the catalyst system, (e) returning the isolated catalyst system to step (a). In the case of this method to practice the present invention, the reaction solvent may be an the olefinic reactant.

Another way to practice the present invention is by removing any volatiles, including reaction products prior to addition of a non-polar solvent. Such a process would occur as follows: (a) reacting an ethylenically unsaturated compound by hydrocyanation in the presence a polar solvent or an excess of the ethylenically unsaturated compound and a catalyst system comprising a zero valent nickel and the ligand of the present invention, (b) removal of volatiles from the reaction media of step (a), (c) dissolving the catalyst system in a non-polar solvent such as a C5 to C20 hydrocarbon solvent so that two layers are formed or adding a two phases solvent mixture to the reaction mixture, (d) isolation of the non-polar solvent containing the catalyst system, (d) evaporation of the hydrocarbon solvent to isolate the catalyst system, (e) returning the isolated catalyst system to step (a) and recovery of either solvent or products distributed in the polar phase.

In another way of practicing the present invention of the invention, the reaction would be run in a two phase reaction solvent. Following reaction, the phase can be separated by conventional means and the product recovered and the catalyst may be recycled for further reaction.

The extraction step in the present invention may be carried out at room temperature and atmospheric pressure or at other conditions that are suitable in the overall processing of batch or continuous hydrocyanation operations. For example, pressures for extraction may be from 0.1 to 1 Pa, with a range of 0.1 to 0.2 Pa being preferred, and temperatures for the extraction may be from 0° to 120° C., with a preferred range from 15° to 50° C.

The preferred way to practice the present invention is to allow the hydrocyanation reaction to take place in an excess of the ethylenically unsaturated compound. Then following the hydrocyanation reaction to add a two phase solvent mixture to partition and extract the reaction products in the polar phase of the solvent mixture and the catalyst system in the non-polar phase.

The process of this invention may be run in either a continuous or batch mode. In general for large scale industrial processes, a continuous mode is preferred while batch mode is more practical for smaller scale reactions.

The invention is illustrated by but not intended to be limited to the following examples.

EXAMPLES

Preparation of Ligand I

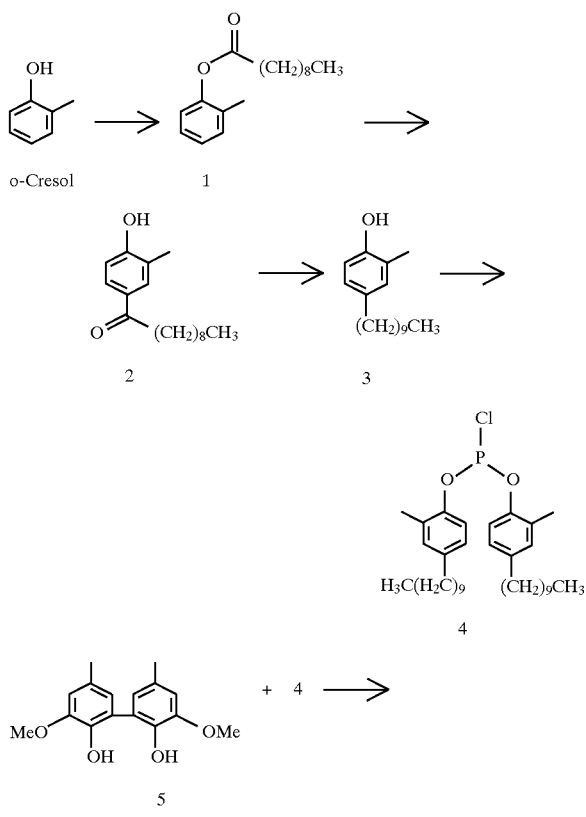

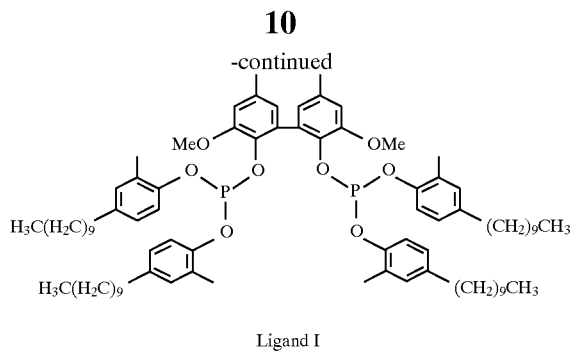

Ligand I

A solution of 109 g (1.08 mol) of triethylamine and 74.4 g (0.688 mol) of o-cresol in 100 mL of diethyl ether was added slowly over a period of three hours to a solution of 130 g (0.682 mol) of decanoyl chloride in 200 mL of diethyl ether. The mixture was stirred at 25° C. for 5 hours and diethyl ether was removed under vacuum. 200 mL of pentane were added, triethylamine hydrochloride filtered and the solvent was evaporated under vacuum to yield 175 g (97%) of 1 as a colorless oil.

A solution of 26 g (0.099 mol) of 1 in 250 mL of nitrobenzene was cooled to 0° C. TiCl$_4$ (38.5 g, 0.203 mol) was added over a 20 minutes period and the solution was stirred for 1 hour at 0° C., then the mixture was allowed to warm to room temperature and stirred overnight. The reaction was quenched by adding 100 mL of 10% HCl. The mixture was extracted with 500 mL of hexane and dried with MgSO$_4$. The solvents were removed under vacuum and the product distilled (140° C. at 0.005 mm Hg) to yield 3.9 g (15%) 2 as a colorless oil.

Zinc (22 g, 0.34 mol) was amalgamated with a solution of 0.475 g (17.5 mmol) of mercuric chloride in 100 mL H$_2$O. The amalgamated zinc was suspended in a mixture of 20 mL of H$_2$O and 20 mL of concentrated HCl and then 3.69 g (14 mmol) of 2, dissolved in 50 mL ethanol were added. The mixture was agitated vigorously and refluxed for 48 hours. The reaction mixture was extracted with toluene and the organic layer extracted with 3 portions of 100 mL of water. The organic layer was dried over MgSO$_4$, the solvent removed under vacuum and the product isolated by high vacuum distillation (130° C. at 0.01 mm Hg). 3 (3 g) was isolated as a colorless oil in 80% yield.

A solution of Cl$_2$PNEt$_2$ (0.347 g, 1.99 mmol) in 50 mL of diethylether was added slowly to a mixture of 3 (0.99 g, 3.99 mmol) and NEt$_3$ (0.515 g, 5.09 mmol) in 50 mL of Et$_2$O. After stirring for 1 hour at room temperature, 3 mL of 1M HCl in Et$_2$O were added and stirring was continued for 15 minutes. The solvent was removed under vacuum and replaced with 50 mL of pentane. The mixture was filtered through celite and the solvent evaporated leaving an oily residue. 4 was isolated as colorless oil (0.47 g) in 42% yield.

A solution of the 5 (0.183 g, 0.668 mmol) and NEt$_3$ (0.268 g, 2.64 mmol) in 20 mL of toluene was added in small portions to a solution of 4 (0.75 g, 1.34 mmol) in 20 mL of toluene. The solvent was removed under vacuum and replaced with 50 mL of pentane. The mixture was filtered through celite and the solvent evaporated in vacuo, leaving an oily residue. The residue was dissolved in 5 mL of CH$_2$Cl$_2$ and filtered through a small pad of neutral alumina.

Ligand I (0.83 g) was isolated as a colorless oil in 94% yield. $^{31}$P{$^1$H} (500 MHz, CD$_2$Cl$_2$):135.5

Preparation of Ligand II

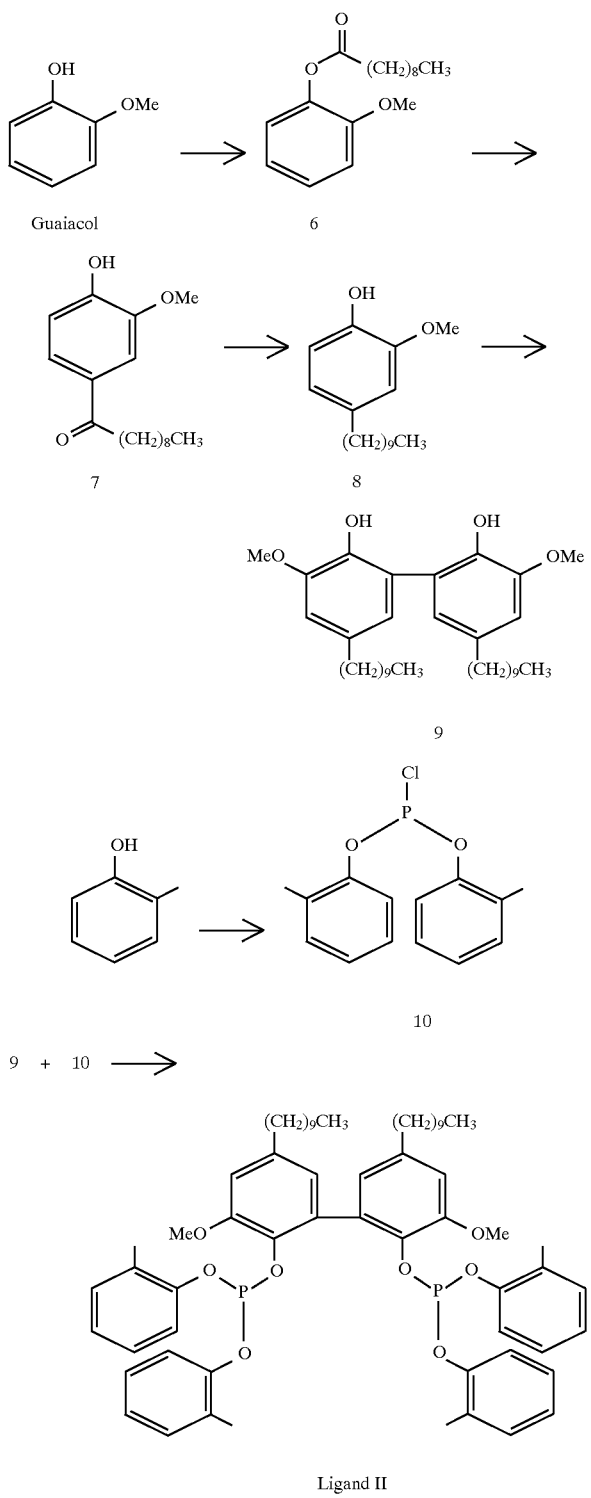

Ligand II

A solution of 35.7 g (0.353 mol) of triethylamine and 38.1 g (0.307 mol) of Guaiacol in 100 mL of diethyl ether was added slowly over a period of three hours to a solution of 58.6 g (0.307 mol) of decanoyl chloride in 200 mL of diethyl ether. The mixture was stirred at 25° C. for 5 hours and diethyl ether removed under vacuum. 200 mL of pentane were added, triethylamine hydrochloride filtered and the solvent was evaporated under vacuum to yield 77.7 g (91%) of 6 as a colorless oil.

A solution of 20.68 g (0.074 mol) of 6 in 200 mL of nitrobenzene was cooled to 0° C. TiCl$_4$ (29.5 g, 0.156 mol) was added over a 20 minutes period and the solution was stirred for 1 hour at 0° C., then the mixture was allowed to warm to room temperature and stirred overnight at room temperature. The reaction was quenched by adding 100 mL of 10% HCl. The mixture was extracted with 500 mL of hexane and dried with MgSO$_4$. The solvents were removed under vacuum and the product distilled (160° C. at 0.005 mm Hg) to yield 6.4 g (31%) 7 as a colorless oil.

Zinc (20 g, 0.306 mol) was amalgamated with a solution of 0.44 g (0.162 mmol) of mercuric chloride in 30 mL H$_2$O. The amalgamated zinc was suspended in a mixture of 20 mL of H$_2$O and 20 mL of concentrated HCl and then 5.79 g (21 mmol) of 7, dissolved in 100 mL ethanol were added. The mixture was agitated vigorously and refluxed for 48 hours. The reaction mixture was extracted with toluene and the organic layer extracted with 3 portions of 100 mL of water. The organic layer was dried over MgSO4, the solvent removed under vacuum and the product isolated by high vacuum distillation (140° C. at 0.005 mm Hg). 8 (5 g) was isolated as a colorless oil in 86% yield.

A solution of 8 (3.76 g, 14.2 mmol) in 75 mL of acetone was combined with 45 mL of H$_2$O and 25 mL of NH$_4$OH (30%), followed by the slow addition of K$_3$Fe(CN)$_6$ (4.9 g, 14.9 mmol) in 20 mL of H$_2$O. The pH of the solution was adjusted to 7 by adding concentrated HCl dropwise and stirring was continued overnight. The solution was extracted with CH$_2$Cl$_2$, the organic layer was extracted with water and dried over MgSO$_4$. The product was purified by column chromatography on silica gel using 15% ethylacetate in hexane as eluent. 9 was isolated as colorless oil (1.57 g) in 42% yield.

A solution of Cl$_2$PNEt$_2$ (0.769 g, 4.42 mmol) in x mL of diethylether was added slowly to a mixture of o-cresol (0.937 g, 8.66 mmol) and NEt$_3$ (0.975 g, 9.64 mmol) in 25 mL Et$_2$O. After stirring for 1 hour at room temperature, 6 mL of 1M HCl in Et$_2$O were added and stirring was continued for 15 minutes. The solvent was removed under vacuum and replaced with 50 mL of pentane. The mixture was filtered through celite and the solvent evaporated leaving an oily residue. 10 was isolated as colorless oil (0.5 g) in 42% yield.

A solution of 9 (1.01 g, 2.0 mmol) and NEt$_3$ (0.678 g, 6.7 mmol) in 10 mL of toluene was added in small portions to a solution of 10 (1.1 g, 4 mmol) in 10 mL of toluene. The solvent was removed under vacuum and replaced with 50 mL of pentane. The mixture was filtered through celite and the solvent evaporated in vacuo, leaving an oily residue. The residue was dissolved in 10 mL of CH$_2$Cl$_2$ and filtered through a small pad of neutral alumina. Ligand II (1.7 g) was isolated as a colorless oil in 82% yield. $^{31}$P{$^1$H} (500 MHz, CD$_2$Cl$_2$):136.

Preparation of Ligand III

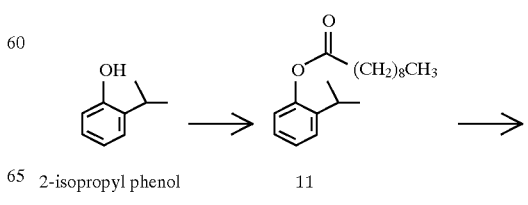

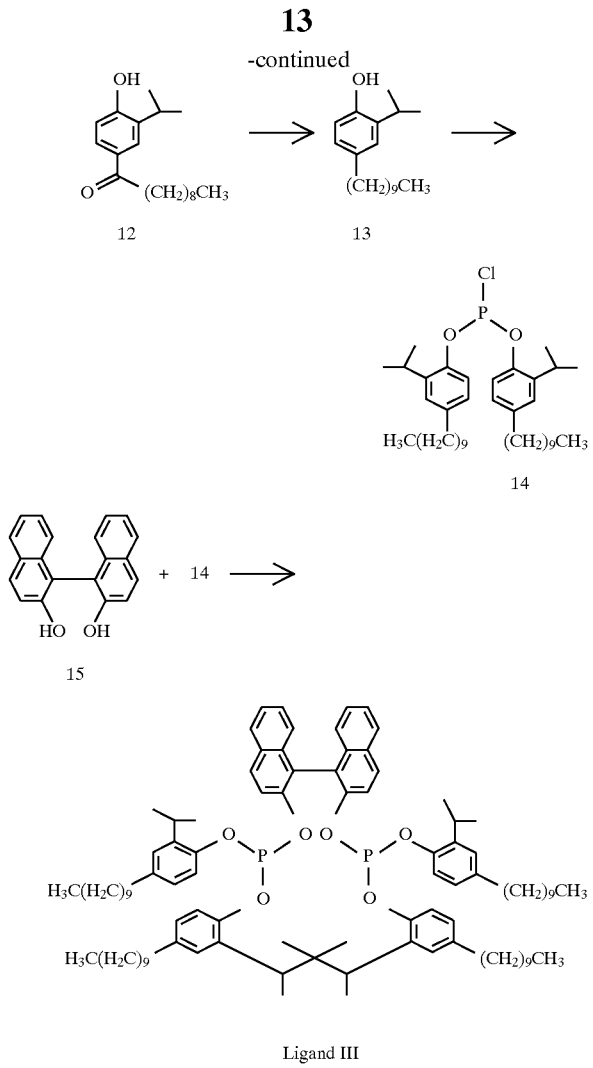

A solution of 32.9 g (0.326 mol) of triethylamine and 39.0 g (0.286 mol) of 2-isopropylphenol in 200 mL diethyl ether was added slowly over a period of three hours to a solution of 54.6 g (0.286 mol) of decanoyl chloride in 300 mL diethyl ether. The mixture was stirred at 25° C. for 5 hours and diethyl ether was removed under vacuum. 200 mL of pentane were added, triethylamine hydrochloride filtered and the solvent was evaporated under vacuum to yield 73.6 g (87%) of 11 as a colorless oil.

A solution of 74 g (0.253 mol) of 11 in 250 mL of nitrobenzene was cooled to 0° C. TiCl$_4$ (96 g, 0.506 mol) was added over a 20 minute period, and the solution was stirred for 1 hour at 0° C., then the mixture was allowed to warm to room temperature and stirred overnight. The reaction was quenched by adding 100 mL of 10% HCl. The mixture was extracted with 500 mL of hexane and dried with MgSO$_4$. The solvents were removed under vacuum and the product distilled (150° C. at 0.005 mm Hg) to yield 12.7 g (17%) 12 as a colorless oil.

Zinc (22 g, 0.34 mol) was amalgamated with a solution of 0.475 g (17.5 mmol) of mercuric chloride in 100 mL H$_2$O. The amalgamated zinc was suspended in a mixture of 20 mL of H$_2$O and 20 mL of concentrated HCl and then 6.1 g (0.021 mmol) of 12, dissolved in 50 mL ethanol, were added. The mixture was agitated vigorously and refluxed for 48 hours. The reaction mixture was extracted with toluene and the organic layer extracted with 3 portions of 100 mL of water.

The organic layer was dried over MgSO$_4$, the solvent removed under vacuum and the product isolated by high vacuum distillation (170° C. at 0.005 mmHg). 13 (5.07 g) was isolated as a colorless oil in 87% yield.

A solution of Cl$_2$PNEt$_2$ (1.59 g, 9.11 mmol) in 50 mL of diethyl ether was added slowly to a mixture of 13 (5.07 g, 18.3 mmol) and NEt$_3$ (2.3 g, 22.7 mmol) in 50 mL of Et$_2$O. After stirring for 1 hour at room temperature, 3 mL of 1M HCl in Et$_2$O were added and stirring was continued for 15 minutes. The solvent was removed under vacuum and replaced with 50 mL of pentane. The mixture was filtered through celite and the solvent evaporated leaving an oily residue. 14 was isolated as colorless oil (8.29 g) in 73% yield.

A solution of 15 (0.252 g, 0.88 mmol) and NEt$_3$ (0.34 g, 3.3 mmol) in 20 mL of toluene was added in small portions to a solution of 14 (1.09 g, 1.76 mmol) in 20 mL of toluene. The solvent was removed under vacuum and replaced with 50 mL of pentane. The mixture was filtered through celite and the solvent evaporated in vacuo, giving Ligand III as an oil in 80% yield. $^{31}$P{$^1$H} (500 MHz, CD$_2$Cl$_2$): 135.

Example 1

Reaction mixtures were heated in a thermostatically controlled oil bath. HCN vapor was delivered to the reaction flask as an HCN/N$_2$ gas mixture by bubbling dry N$_2$ gas through liquid HCN maintained at 0° C. in a wet ice bath. This provided a vapor stream which was roughly 35% HCN (vol/vol). The rate of HCN delivery was adjusted by varying the rate of N$_2$ flow. Sample analyses were done by gas chromatography using a DB-23 capillary column.

500 mg of Ligand (I or II), 40 mg of Ni(COD)$_2$ and 20 mg of ZnCl$_2$ were dissolved in 5 mL of 3-pentenonitrile. The mixture was treated with HCN at a nitrogen flow rate of 30 mL/min at 70° C. for one hour. GC analysis indicated:

Ligand I: 61% Conversion, 91% Selectivity to ADN
Ligand II: 83% Conversion, 93% Selectivity to ADN Catalyst Recycle:

The product mixture obtained as described before was extracted three times with 20 mL of pentane. The combined pentane extracts were combined and the solvent removed under vacuum. 3-pentenonitrile (5 mL) and ZnCl$_2$ (20 mg) were added and the mixture was treated again with HCN under the same conditions described before. GC analysis indicated:

Ligand I: 61% Conversion, 91% Selectivity to ADN
Ligand II: 83% Conversion, 93% Selectivity to ADN

What is claimed:

1. A process for hydrocyanation comprising reacting a nonconjugated, ethylenically unsaturated compound in a reaction solvent with HCN in the presence of a Lewis acid promoter and a catalyst system comprising a zero valent nickel compound and an organic phosphorous containing ligand having the structure (PR$_2$)$_n$R' where n is an integer from 1 to 2, R and R' are organic groups which are the same or different and where the R or R' have at least one C9 to C40 aliphatic group positioned as a tail extending away from the primary ligand structure rendering the ligand lipophilic and wherein the reaction solvent is a two phase mixture of an organic compound having from 5 to 20 carbon atoms and polar solvent and wherein reaction products are recovered from the polar phase of the reaction solvent and the catalyst is in the non-polar phase of the reaction solvent.

2. The process of claim 1 wherein the ligand is a bidentate phosphite.

3. A process for hydrocyanation of an a nonconjugated, ethylenically unsaturated compound wherein reaction products including high boiling reaction products are easily separated from the catalyst system comprising the steps of:

(a) reacting the ethylenically unsaturated compound in a polar reaction solvent to form a reaction mixture with HCN in the presence of Lewis acid promoter and a catalyst system composed of a zero valent nickel compound and an organic phosphorous containing ligand having the structure $(PR_2)_nR'$ where n is an integer from 1 to 2, R and R' are organic groups which are the same or different and where the R or R' contain at least one C9 to C40 aliphatic group positioned as a tail extending away from the primary ligand structure rendering the ligand lipophilic;

(b) adding a non-polar solvent to the reaction mixture to form two phases, one a polar phase predominately formed from the reaction products and one formed predominately from the non-polar solvent and the catalyst system where the reaction products including the high boiling reaction products of the hydrocyanation remain in the polar phase and the catalyst system is partitioned substantially into the non-polar phase; and (c) separating the two phases and isolating the reaction products from the polar phase and the catalyst from the non-polar phase.

4. The process of claim 3 wherein volatiles are removed from the reaction mixture of step (a) before the addition of the polar solvent of step (b).

5. The process of claim 3 wherein steps (a) and (b) are combined and the hydrocyanation is carried out in a two phase reaction solvent.

6. The process of claim 3 wherein the recovered catalyst is returned to step (a) and the steps are repeated.

7. The process of claim 1 or 3 wherein the non-polar solvent is chosen from the group of C5 to C20 hydrocarbon solvents.

8. The process of claim 1 or 3, wherein the ethylenically unsaturated compound is chosen from the group consisting of 3-pentenenitrile, 4-pentenenitrile and alkyl-3-pentenoate.

9. The process of claim 1 or 3 wherein the organic ligand is chosen from the structures.

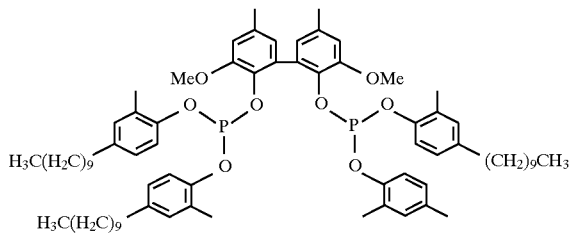

Ligand I

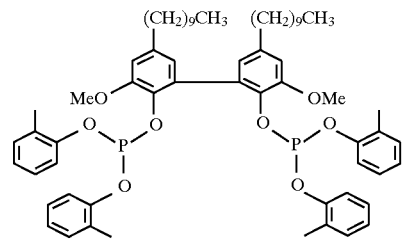

Ligand II

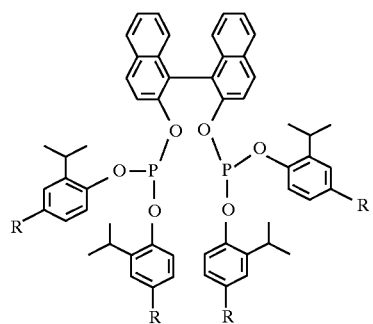

Ligand III wherein Ligand III R is either $CO(CH_2)_8CH_3$ or $(CH_2)_9CH_3$.

10. An improved hydrocyanation process where a nonconjugated, ethylenically unsaturated compound is reacted with HCN in the presence of a Lewis acid promoter and a catalyst system composed of a zero valent nickel compound and a bidentate organic phosphorous containing ligand wherein the ethylenically unsaturated compound also functions as reaction solvent, the improvement comprising: forming the catalyst system from the ligand having the structure $(PR_2)_nR'$ where n is an integer from 1 to 2, R and R' are organic groups which are the same or different and where the R or R' have at least one C9 to C40 aliphatic group positioned as a tail extending away from the primary ligand structure rendering the ligand lipophilic; and following hydrocyanation of the ethylenically unsaturated compound adding to the reaction mixture a two phase solvent mixture consisting of a polar and a non-polar phase so that the reaction products of the hydrocyanation are extracted into the polar phase of the solvent mixture and the catalyst system remains substantially in the non-polar phase of the solvent mixture.

11. The process of claim 10 wherein the non-polar solvent is chosen from the group of C5 to 20 hydrocarbon solvents.

12. The process of claim 10, wherein the ethylenically unsaturated compound is chosen from the group consisting of 3-pentenenitrile, 4-pentenenitrile and alkyl-3-pentenoate.

13. The process of claim 10 wherein the ligand is a bidentate phosphite.

14. The process of claim 10 wherein the organic ligand is chosen from the structures

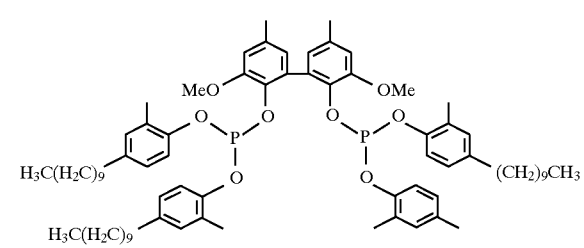

Ligand I

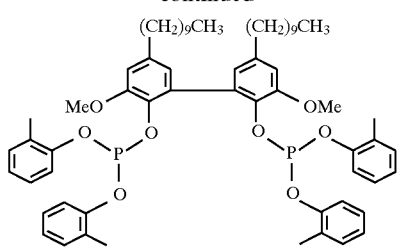
Ligand II
and
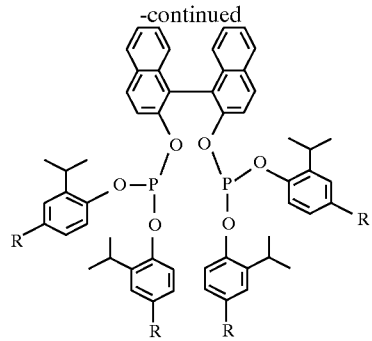
Ligand III
wherein Ligand III R is either $CO(CH_2)_8CH_3$ or $(CH_2)_9CH_3$.
* * * * *